(12) United States Patent
Nishigishi

(10) Patent No.: US 10,850,010 B2
(45) Date of Patent: Dec. 1, 2020

(54) STENT

(71) Applicant: PENTAS Inc., Tokyo (JP)

(72) Inventor: Makoto Nishigishi, Tokyo (JP)

(73) Assignee: PENTAS Inc., Tokyo (JP)

( * ) Notice: Subject to any disclaimer, the term of this patent is extended or adjusted under 35 U.S.C. 154(b) by 81 days.

(21) Appl. No.: 16/075,367

(22) PCT Filed: Feb. 22, 2017

(86) PCT No.: PCT/JP2017/006518
§ 371 (c)(1),
(2) Date: Aug. 3, 2018

(87) PCT Pub. No.: WO2017/146080
PCT Pub. Date: Aug. 31, 2017

(65) Prior Publication Data
US 2019/0046694 A1 Feb. 14, 2019

(30) Foreign Application Priority Data
Feb. 25, 2016 (JP) .................... 2016-033783

(51) Int. Cl.
| *A61F 2/88* | (2006.01) |
| *A61L 31/02* | (2006.01) |
| *A61L 31/14* | (2006.01) |
| *A61F 2/90* | (2013.01) |

(52) U.S. Cl.
CPC ............. *A61L 31/022* (2013.01); *A61F 2/88* (2013.01); *A61F 2/90* (2013.01); *A61L 31/14* (2013.01)

(58) Field of Classification Search
CPC ..................................... A61F 2/88; A61F 2/90
USPC ................................................ 623/1.5–1.53
See application file for complete search history.

(56) References Cited

U.S. PATENT DOCUMENTS

| 5,741,325 A * | 4/1998 | Chaikof | A61F 2/90 623/1.35 |
| 5,843,175 A * | 12/1998 | Frantzen | A61F 2/91 623/1.15 |
| 7,438,712 B2 * | 10/2008 | Chouinard | A61F 2/07 604/527 |
| 9,039,754 B2 * | 5/2015 | Nishigishi | A61F 2/90 623/1.22 |
| 10,470,902 B2 * | 11/2019 | Sheldon | B23K 26/20 |
| 2009/0054972 A1 * | 2/2009 | Norton | D04C 1/06 623/1.53 |
| 2012/0265294 A1 | 10/2012 | Nishigishi | |
| 2013/0204350 A1 * | 8/2013 | Richter | A61F 2/91 623/1.16 |

(Continued)

FOREIGN PATENT DOCUMENTS

| DE | 102015107291 A1 | 9/2015 | |
| DE | 102015107291 B4 * | 6/2017 | ............... A61F 2/90 |
| JP | 2012223209 A | 11/2012 | |

OTHER PUBLICATIONS

International Search Report dated May 16, 2017 filed in PCT/JP2017/006518.

*Primary Examiner* — Suzette J Gherbi
(74) *Attorney, Agent, or Firm* — Rankin, Hill & Clark LLP

(57) ABSTRACT

Some of strands of a stent are disposed using a strand made of a platinum alloy material. In the stent (10) formed by helicoidally braiding a plurality of strands, some even-numbered strands among the plurality of strands are disposed using a platinum alloy material.

16 Claims, 3 Drawing Sheets

(56) References Cited

U.S. PATENT DOCUMENTS

| | | | |
|---|---|---|---|
| 2013/0282108 A1* | 10/2013 | Houston | B29C 45/14622 |
| | | | 623/1.22 |
| 2014/0288637 A1 | 9/2014 | Clerc | |
| 2016/0143754 A1* | 5/2016 | Orion | A61F 2/82 |
| | | | 623/1.15 |
| 2016/0175085 A1* | 6/2016 | Johnson | A61F 2/01 |
| | | | 606/200 |
| 2018/0271682 A1* | 9/2018 | Treacy | A61F 2/88 |
| 2018/0272044 A1* | 9/2018 | Hossainy | A61F 2/966 |
| 2019/0046340 A1* | 2/2019 | Nishigishi | A61F 2/90 |
| 2019/0133800 A1* | 5/2019 | Krolik | A61F 2/958 |
| 2019/0201218 A1* | 7/2019 | Shobayashi | A61F 2/89 |
| 2019/0262151 A1* | 8/2019 | Treacy | A61F 2/90 |
| 2019/0365548 A1* | 12/2019 | Sirhan | A61F 2/89 |

\* cited by examiner (A)

(B)

STENT

TECHNICAL FIELD

The present invention relates to a stent.

BACKGROUND ART

There is known a stent for medical purpose as follows. The stent is formed by helicoidally braiding a plurality of strands (see Patent Literature 1).

CITATION LIST

Patent Literature

Patent Literature 1: JP 2012-223209 A

SUMMARY OF THE INVENTION

Technical Problem

In recent years, a stent formed by helicoidally braiding a plurality of strands is used for the purpose of medical treatment of an aneurysm. As a strand of the stent, metal strands such as a stainless steel, a Co—Cr alloy (cobalt-chromium alloy), a Ni—Ti alloy (nickel-titanium alloy) are generally used. These materials have a transmissive property with respect to an X ray. Therefore, the stent implanted in a blood vessel of a patient may be not captured at the time of an X-ray photography, and thus it is not possible to check the implantation position of the stent of the patient. In order to solve the problem, it has been considered that the stent is made of a platinum alloy material having a non-transmissive property with respect to the X ray. However, the strand made of the platinum alloy material is degraded in an extending performance compared to a typical strand. Therefore, when the number of strands made of the platinum alloy material in the stent is set to an odd number, there is a concern that the stent does not evenly extend. However, the related art fails in studying a method of determining, the number of strands made of the platinum alloy material in consideration of the problem.

Solution to Problem

According to a first aspect of the invention, the stent is formed by helicoidally braiding a plurality of strands. Some even-numbered strands among the plurality of strands are disposed using a strand made of a platinum alloy material.

According to a second aspect of the invention, the stent of the first aspect is configured such that two strands among the plurality of strands are disposed using a strand made of the platinum alloy material.

According to a third aspect of the invention, the stent of the first or second aspect is configured such that strands in the same winding direction among the plurality of strands are disposed using the strand made of the platinum alloy material.

According to a fourth aspect of the invention, the stent of the first to third aspects is configured such that the plurality of strands are strands made of a cobalt-chromium alloy material, and the strand made of the platinum alloy material is a strand made of a platinum-iridium alloy material.

Advantageous Effects of Invention

According to the invention, some even-numbered strands among the plurality of strands are disposed using a strand made of a platinum alloy material, so that it is possible to make the stent extend evenly when the stent extends.

DESCRIPTION OF EMBODIMENTS

Figure 1:
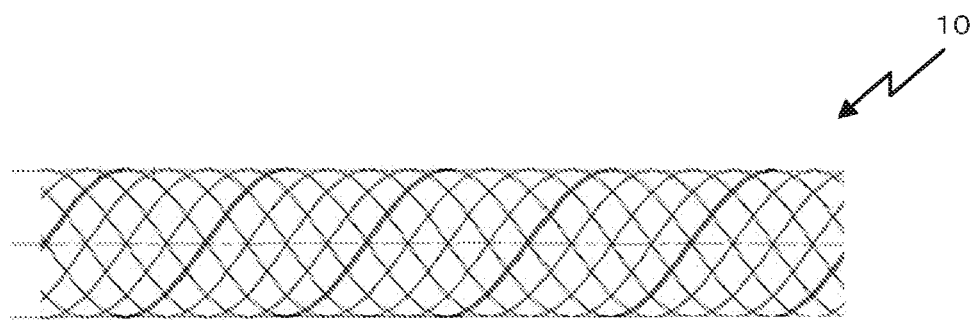
FIG. 1 is a diagram schematically illustrating a shape of a stent formed by helicoidally braiding a plurality of strands.

FIG. 1 is a diagram schematically illustrating a shape of a stent in the embodiment. In the embodiment, a stent 10 is assumed to be formed by helicoidally braiding a plurality of strands as illustrated in FIG. 1. In the strand, for example, a metal material such as a stainless steel, a Co—Cr alloy (cobalt-chromium alloy), and a Ni—Ti alloy (nickel-titanium alloy) is used.

The stent 10 is formed by helicoidally braiding a plurality of metal strands. The number of strands of the stent 10 has a plurality of types. For example, a 16-strand stent formed by braiding 16 strands, a 24-strand stent formed by braiding 24 strands, and a 32-strand stent formed by braiding 32 strands. Further, FIG. 1 illustrates the 16-strand stent.

In the stent 10 formed by helicoidally braiding the plurality of metal strands, the metal strand has a transmissive property with respect to an X ray. Therefore, at the time of an X-ray photography, the stent in a patient cannot be captured, and the implantation position of the stent of the patient cannot be checked. In the stent of the embodiment to solve such a problem, some strands among the plurality of strands of the stent are disposed using a strand made of a platinum alloy material having a non-transmissive property with respect to the X ray.

The embodiment will be described about a case where the strands (hereinafter, referred to as "Pt—Ir strand") made of a platinum-iridium alloy material are disposed such that a plurality of the strands (for example, 2 adjacent strands) are adjacent in the stent configured by strands (hereinafter, referred to as "Co—Cr strands") made of the cobalt-chromium alloy.

Figure 2:
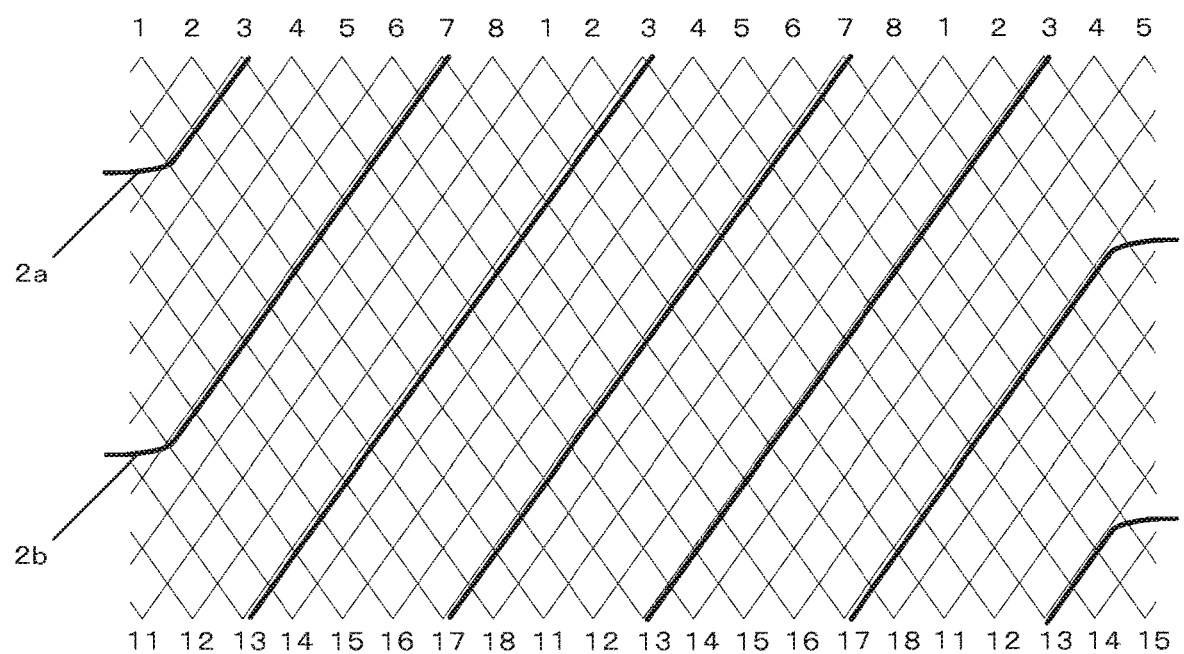
FIG. 2 is a diagram schematically illustrating an exemplary layout of a platinum alloy wire in a developed view of the stent.

FIG. 2 is a diagram schematically illustrating an exemplary layout of the Pt—Ir strands in a developed view of the 16-strand stent. In the example illustrated in FIG. 2, eight strands are braided in a first direction inclined on a right upper side and a second direction inclined on a left upper side. In FIG. 2, the numbers attached in the upper and lower portion of the developed view are only attached for the convenience' sake in order to help with understanding that the strands are continuously disposed, and there is no other meaning. The numbers attached on the upper portion of the developed view indicate that the strands are continuously disposed in the first direction inclining on the right upper side in FIG. 2. For example, the same number on the upper portion indicates one strand which is wound in the first direction. In addition, the number attached on the lower portion of the developed view indicates that the strands wound in the second direction inclined on the left upper side in FIG. 2 are continuously disposed. For example, the strands attached with the same number in the lower portion indicate one strand which is wound in the second direction.

In the embodiment, the even-numbered strands in the same winding direction among the Co—Cr strands of the stent are disposed using the Pt—Ir strands. In FIG. 2, a Pt—Ir strand 2a depicted with a thick line is disposed at a strand 3 wound in the first direction. A Pt—Ir strand 2b depicted with a thick line is disposed at a strand 7 wound in the first direction. In other words, in FIG. 2, two Pt—Ir strands 2a and 2b are disposed with respect to the Co—Cr strand 3 and the Co—Cr strand 7 wound in the first direction. In this way, it is preferable that two Pt—Ir strands be disposed in the stent as illustrated in FIG. 2 from the viewpoint of an even extending performance and an even extending force of the stent.

Herein, the description will be given about the reason why two Pt—Ir strands are disposed in the stent. Compared to the Co—Cr strand, a surface having the extending performance of the Pt—Ir strand is degraded. Therefore, the extending force of the stent can be secured as the number of the Pt—Ir strands disposed in the stent becomes small. In addition, when the number of the Pt—Ir strands disposed in the stent is set to an odd number, there is a concern that the stent does not extend evenly. Therefore, it can be said that an even number or two satisfying a condition as small as possible are optimal to the number of Pt—Ir strands.

Figure 3:
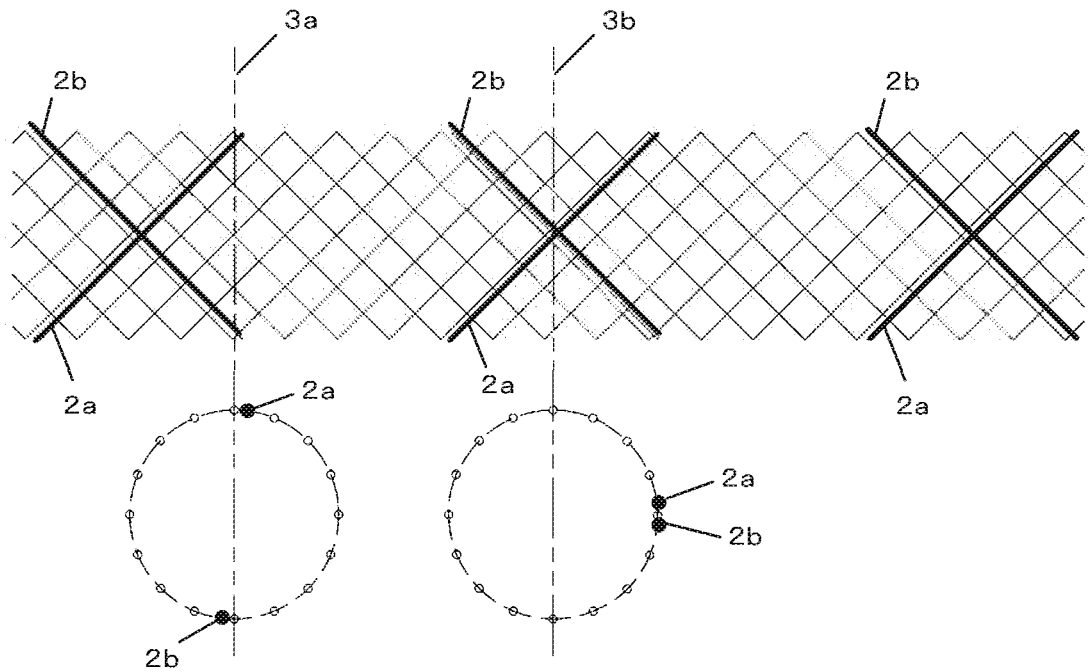
FIG. 3 is a diagram schematically illustrating an exemplary layout of the platinum alloy wire in a side view of the stent.
Figure 3:
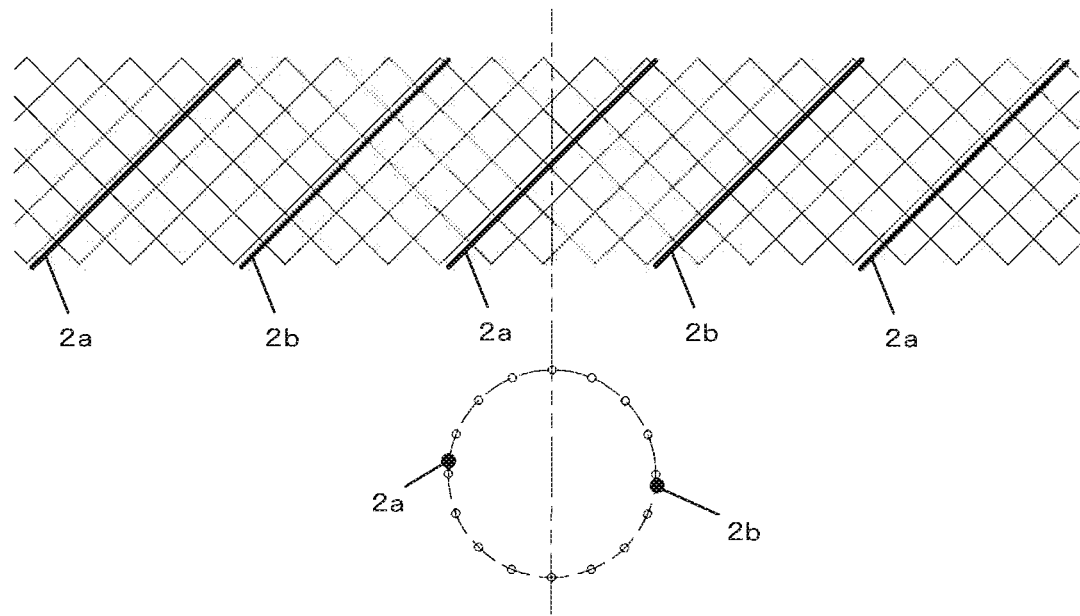

In addition, as illustrated in FIG. 2, the reason why two Pt—Ir strands are wound in the same direction is as follows. In a case where two Pt—Ir strands are disposed in different winding directions, an interval of two Pt—Ir strands is different depending on a portion of the stent as illustrated in FIG. 3(a). In other words, the interval between two Pt—Ir strands 2a and 2b is widened at a position 3a on the stent as illustrated in FIG. 3(a), but the interval between two Pt—Ir strands 2a and 2b becomes narrow at a position 3b. At a position where the interval between two Pt—Ir strands 2a and 2b becomes narrow as the position 3b, a portion between the Pt—Ir strands 2a and 2b is plastically deformed. Therefore, a cross-sectional shape of the stent at the position 3a and a cross-sectional shape of the stent at the position 3b are different. In this way, in a case where two Pt—Ir strands are disposed in different winding directions, the cross-sectional shape of the stent is changed depending on a position on the stent.

On the contrary, in a case where two Pt—Ir strands are disposed in the same winding direction at an equal interval, the interval between two Pt—Ir strands 2a and 2b is not changed regardless of a position as illustrated in FIG. 3(b). Therefore, the cross-sectional shape is not changed depending on a position on the stent. In the embodiment, two Pt—Ir strands 2a and 2b are disposed in the same winding direction, so that it is prevented that the cross-sectional shape is changed depending on a position on the stent.

According to the embodiment, the following operational effects can be obtained.

(1) In a stent which is formed by helicoidally braiding a plurality of strands, some even-numbered strands among the plurality of strands are disposed using, a PT-Ir strand made of a platinum alloy material. With this configuration, since platinum has a non-transmissive property with respect to the X ray, it is possible to check an implantation position of the stent at the time of an X-ray photography. Further, it is possible to make the stent extend evenly when the stent extends.

(2) Two strands among the plurality of strands are disposed using a Pt—Ir strand. With this configuration, it is possible to dispose the Pt—Ir strands to make the stent extend evenly after an extending force of the stent is secured.

(3) Strands in the same winding direction among the plurality of strands are disposed using the Pt—Ir strands. With this configuration, it is possible to secure the same cross-sectional shape regardless of a position on the stent.

Modifications

Further, the stent of the embodiment may be modified as follows.

(1) In the above-described embodiment, the Pt—Ir strands made of a platinum-iridium alloy material are disposed as two strands made of a platinum alloy material disposed in the stent. However, the strand is not limited to the Pt—Ir strand as long as the material is suitable to dispose the stent and an alloy containing platinum having a non-transmissive property with respect to the X ray is used.

Further, the invention is not limited to any one of the configurations of the above-described embodiment as long as the characteristic functions of the invention are not degraded.

Priority is claimed on Japanese Patent Application No. 016-33783 filed on Feb. 25, 2016, the content of which is incorporated herein by reference.

REFERENCE SIGNS LIST 10 stent
2a first platinum alloy wire
2b second platinum alloy wire

The invention claimed is:

1. A stent which is formed by helicoidally braiding a plurality of strands,
   wherein an even number of strands made of a platinum alloy material are disposed with respect to an even number of strands in a same winding direction among the plurality of strands, and
   wherein an interval of the even number of strands made of the platinum alloy material is constant in a radial cross section of the stent.

2. The stent according to claim 1,
   wherein the even number is two.

3. The stent according to claim 1,
   wherein the plurality of strands are strands made of a cobalt-chromium alloy material, and
   wherein the strand made of the platinum alloy material is a strand made of a platinum-iridium alloy material.

4. The stent according to claim 1,
   wherein the even number of strands made of the platinum alloy material are disposed at an equal interval.

5. A stent comprising:
   a plurality of strands helicoidally braided to form the stent; and
   an even number of platinum alloy strands,
   wherein each of the even number of platinum alloy strands is disposed adjacent to one of the plurality of strands,
   the even number of platinum alloy strands are wound in a same winding direction, and
   an interval of the even number of the platinum alloy strands is constant in a radial cross section of the stent.

6. The stent according to claim 5,
   wherein the even number is two.

7. The stent according to claim 5,
   wherein the plurality of strands are strands made of a cobalt-chromium alloy material, and
   wherein the even number of platinum alloy strands are strands made of a platinum-iridium alloy material.

8. The stent according to claim 5,
wherein the even number of platinum alloy strands are disposed at an equal interval.

9. The stent according to claim 1,
wherein a winding direction of all of the strands made of the platinum alloy material is the same.

10. The stent according to claim 5,
wherein a winding direction of all of the platinum alloy strands is the same.

11. The stent according to claim 1,
wherein a total number of the strands made of the platinum alloy material in the stent is the even number.

12. The stent according to claim 5,
wherein a total number of the platinum alloy strands in the stent is the even number.

13. The stent according to claim 11,
wherein a winding direction of all of the strands made of the platinum alloy material is the same.

14. The stent according to claim 12,
wherein a winding direction of all of the platinum alloy strands is the same.

15. The stent according to claim 1,
wherein a total number of the strands made of the platinum alloy material in the stent is two, and
wherein a winding direction of all of two of the strands made of the platinum alloy material is the same.

16. The stent according to claim 5,
wherein a total number of the platinum alloy strands in the stent is two, and
wherein a winding direction of all of two of the platinum alloy strands is the same.

* * * * *